United States Patent [19]

Drakoff

[11] 4,375,465
[45] Mar. 1, 1983

[54] COSMETIC PRESERVATIVE

[75] Inventor: Raymond Drakoff, New York, N.Y.

[73] Assignee: Lever Brothers Company, New York, N.Y.

[21] Appl. No.: 275,472

[22] Filed: Jun. 19, 1981

[51] Int. Cl.³ .................... A61K 31/00; A61K 31/85; A61K 47/00
[52] U.S. Cl. .................................. 424/175; 424/315; 424/358
[58] Field of Search .................... 424/358, 175, 315

[56] References Cited
U.S. PATENT DOCUMENTS 3,132,993  5/1964  Granatek ............................ 424/175

OTHER PUBLICATIONS

Ash et al. "A Formulary of Cosmetic Preparations" pp. 31, 32, 124. Chemical Publishing Co. NY., NY.

Balsam et al. "Cosmetics Science and Technology" vol. 3, pp. 391–394, 453–457, John Wiley & Sons, N.Y.
"Sodium Formaldehyde Bisulphite" Technical Bulletin, Millmaster Chemical Company.
Merck Index, 9th Ed., 1976, p. ONR-57.

*Primary Examiner*—Stanley J. Friedman
*Attorney, Agent, or Firm*—James J. Farrell

[57] ABSTRACT

This invention reveals the preparation of aqueous preservative cosmetics subject ot Maillard reaction employing sodium hydroxymethane sulfonate which provides a time released sterilizing and anti-browning effect in cosmetic compositions containing amino or nitro groups, polyhydroxy compounds or sugars and having a pH of about 7.0 or higher. Potassium, ammonium and other cationic forms of hydroxymethane sulfonate and mixtures thereof may also be employed.

7 Claims, No Drawings

COSMETIC PRESERVATIVE

This invention relates generally to preservatives and more particularly to cosmetic preservatives. It deals with the composition of novel preservative cosmetics and discloses a new use of a known compound. Specifically involved is a time-released preservative put into cosmetic compositions susceptible to bacterial attack and to browning in color which these compositions frequently undergo.

Marketed cosmetics, not self-preserving, contain ingredient(s) which stop microbial proliferation thereby protecting the cosmetic from degradation and malodor and protecting the consumer from the problems attending microbial contamination. Cosmetics may also turn brown (Maillard reaction) over a period of time if they contain amino or nitro groups and polyhydroxy compounds and sugars.

Formaldehyde and sodium bisulfite are known and used as separate ingredients for overcoming the problems of bacterial contamination and browning due to the Maillard reaction. However, formaldehyde is rather a reactive compound with an undesirable odor. It has a quick knock-out action upon the flora of the system which is thereby rendered sterile; then this preservative, in the concentration usually employed in cosmetic preparations, virtually disappears. Because formaldehyde is so reactive, it can often be consumed by other ingredients thus losing its biocidal properties. Later, during the course of bottling the preparation or when the product is opened and in use by the consumer, the bacteria find their way back into the container and the decay, degradation or putrefaction of the product resumes.

Sodium bisulfite is a water-soluble antioxidant. Like formaldehyde, its activity is immediately available. Also, like formaldehyde, it is a reactive molecule especially with atmospheric oxygen and its activity decreases rapidly with time. As the bisulfite ion is oxidized, its inhibitory effect upon the browning (Maillard) reaction correspondingly abates, the browning reaction resumes and the system discolors toward yellow and then to brown.

There are a number of chemicals in the marketplace which claim to be slow formaldehyde releasers, metering out biocidal or antimicrobial activity over a period of time. It should be noted, however, that these marketed products are rather expensive and have only one area of activity, namely, they are biocides or sterilants. They do not possess a simultaneous antioxidant (anti-browning) action similar to that of sodium bisulfite. Slow bisulfite releasers which will meter out anti-browning effect over an extended period of time are commonly not known in the commercial use.

It is, therefore, an object of this invention to provide a preservative having simultaneous dual properties of acting against microflora as well as against browning due to Maillard reaction.

It is another object of this invention to provide a rather inexpensive, time-released, colorless, odorless, water-soluble preservative suitable for use in aqueous cosmetics having a neutral to an alkaline pH. The term aqueous as used herein means water containing. Other objects and advantages will appear as the description proceeds.

Sodium hydroxymethane sulfonate, also known chemically as sodium formaldehyde bisulfite, $NaCH_3OSO_3$, is a white, water-soluble rather inexpensive powder which forms colorless and odorless solutions. Under alkaline conditions this compound is believed to slowly hydrolyze into formaldehyde and sodium bisulfite which by their presence render the desired antibacterial and antioxidant preservative properties, respectively. A preservative aqueous cosmetic composition having an antioxidant and an antibacterial property imparted by a single component is, therefore, obtained by treating the cosmetic composition with a sufficient amount of sodium hydroxymethane sulfonate to exert a preservative effect to the cosmetic formulation when the pH of the formulation is about 7.0 or higher. Although the sodium salt of hydroxymethane sulfonate is the compound of choice, other salts of hydroxymethane sulfonate wherein the cation is selected from the group consisting of potassium, ammonium and the like and mixtures thereof, may also be employed according to the teaching of the present invention.

Corn syrups, honey and polyglycols, many of which are inexpensive, possess properties including that of being humectants, which render them useful in cosmetic preparations. The slow, time-released, anti-browning property together with the anti-microbial activity of the compound of the present invention makes it possible to prepare cosmetic formulations wherein said formulation has corn syrup as an ingredient. It is, therefore, another object of this invention to provide a preservative cosmetic formulation using corn syrup or polyol material as an ingredient or indeed any formulation subject to the Maillard reaction.

The attainment of the above objects is made possible by this invention, which includes a cosmetic composition susceptible to bacterial action and browning which comprises sodium hydroxymethane sulfonate in an amount sufficient to produce a preservative effect and an aqueous cosmetic formulation having a pH value of about 7.0 or higher.

The following examples will more fully illustrate the embodiments of this invention. It may be noted that the blending of various ingredients shown in the examples set forth below is accomplished by methods well known in the art and is not a part of this invention. Use has been made of the standard CTFA Cosmetic Ingredient Dictionary (1973) published by the Cosmetic, Toiletry and Fragrance Association, Washington, D.C. for the nomenclature of certain ingredients listed in the examples set forth herein. In these examples, as well as in the specification and appended claims, parts and percent are by weight unless otherwise indicated.

EXAMPLE 1

The following is an illustration of a cosmetic formulation useful either as a skin cleanser, a bubble bath, a hair cosmetic, and for other similar purposes according to the present invention.

TABLE I

A CLEANSING COSMETIC

| Essential Ingredients | Preferred Range % | Broad Range % |
|---|---|---|
| Polyol(s) (Corn syrups, sugars, glycerol) | 5–35 | 1–60 |
| Nitro Compounds* (Quaternium 19) | 0.1–1.5 | Trace–5 |
| Sodium Hydroxymethane Sulfonate ($NaCH_3OSO_3$) | 0.05–1.0 | 0.01–3 |
| Detergent* (Triethanolamine lauryl sulfate) | 5–25 | 0.2–35 |

TABLE I-continued
A CLEANSING COSMETIC

| Essential Ingredients | Preferred Range % | Broad Range % |
|---|---|---|
| Foam Booster* (Fatty acid alkanolamide) | 0.5–5 | 0–15 |
| Conditioners* (Quaternium 19, Dimethicones, gums, waxes, oils, proteins, resins, etc.) | 0.1–6 | 0–10 |
| Thickeners* (Carbomer 940, hydroxylpropylmethyl- cellulose, Quaternium 19, Salt, etc.) | 0–3 | 0–5 |
| Fragrance* | 0.1–2 | 0–5 |
| Color(s) | 0.01–0.5 | 0–2 |
| Water | to make 100% | to make 100% |
| pH | 7.0–10 | 7.0–12 |

*NOTE:
Real source of nitro compounds may be any material and the example is not limited to the nitro category cited (Triethanolamine is a potential source, trace amines in the foam booster, proteins and nitrogeneous resins, oils, etc., may also be a source; same is true for thickeners, fragrance, etc.)

It will be understood, of course, by those skilled in the art that the preservative effectiveness will depend in large measure upon the quantity of materials to be preserved. A reduction of the concentration of polyols and nitro containing compounds, such as shown in Table I, will correspondingly reduce the need for the preservative component and vice versa. However, it should be noted that there is a lower limit, e.g. about 0.01%, below which there is insufficient preservative component to inhibit the undesirable effects.

EXAMPLE 2

A liquid shampoo formulation according to the present invention is disclosed in Table II.

TABLE II
LIQUID SHAMPOO

| Chemical Identity | Percent in Formula |
|---|---|
| Corn syrup 42 dextrose equivalent | 21.00 |
| Acrylic carboxypolymer | 0.75 |
| Hydroxypropylmethylcellulose | 0.25 |
| 40% triethanolamine lauryl sulfate | 40.00 |
| Cocoamide MEA | 3.00 |
| Quaternium 19 | 0.50 |
| Denatured Ethanol | 9.00 |
| Perfume | 0.50 |
| Triethanolamine | 2.50 |
| Sodium Formaldehyde Bisulfite | 0.25 |
| D & C Yellow #10 | 0.011 |
| Deionized Water | to make 100% |
| pH is 7.0–7.5 | |

It should be pointed out that there are no limitations in incorporating sodium hydroxymethane sulfonate according to the teaching of the present invention in any cosmetic formulation where the use of sodium bisulfite or of formaldehyde or a mixture thereof would otherwise be indicated. Such contemplated compositions which will fall within the scope of this invention, wherein the humectant may be the corn syrup, or other polyols susceptible to browning, are: moisturizing creams, cleansing creams, hand creams, foundation creams, massage creams, lotions, gels, bath products, liquid and bar soaps, face makeups, eye makeups, antiperspirants, roll-ons, sticks, hair creams, hair conditioners, hair dressings, cream rinses, wave sets, wave permanents, suntan preparations, facial gels, masques, pastes and the like. As a further illustration of the utility of the present invention, examples of a gel cosmetic formulation and of a cream are presented in Table III and IV, respectively.

TABLE III
GEL COSMETIC FORMULATION

| Chemical Identity | Percent in Formula |
|---|---|
| Corn syrup 36 dextrose equivalent | 8.00 |
| Acrylic carboxypolymer | 1.05 |
| Hydroxypropylmethylcellulose | 1.25 |
| 40% Triethanolamine lauryl sulfate | 55.00 |
| Cocoamide MEA | 4.20 |
| Quaternium 19 | 0.70 |
| Denatured Alcohol | 8.75 |
| Perfume Oil | 0.50 |
| Sodium Formaldehyde Bisulfite | 0.25 |
| Triethanolamine | 3.50 |
| Certified Dye 1 | 0.01 |
| Deionized Water | to make 100% |
| pH is 7.0–7.5 | |

TABLE IV
CREAM FORMULA

| Chemical Identity | Percent in Formula |
|---|---|
| Partially ethoxylated fatty alcohols | 6.0 |
| Bees Wax | 1.0 |
| Light mineral oil | 2.0 |
| Liquid Lanolin | 1.0 |
| Isopropyl myristate | 1.0 |
| Triethanolamine | 1.0 |
| Propylene glycol | 2.0 |
| Corn syrup 36 dextrose equivalent | 20.0 |
| Perfume | 0.2 |
| Sodium hydroxymethane sulfonate | 0.5 |
| Water | 65.3 |
| | 100.0 |
| pH is 8.7 | |

In order to demonstrate the advantage, utility and effectiveness of sodium hydroxymethane sulfonate as a preservative in cosmetic preparations, prototype formulations were prepared as shown in Table V.

TABLE V
PERCENT COMPOSITION OF PROTOTYPE SHAMPOO

| | Control (Blank) | Combined Mix* | NaCH$_3$OSO$_3$ |
|---|---|---|---|
| 40% Triethanolamine Lauryl sulfate (#N-8298) | 40.00 | 40.00 | 40.00 |
| Western N.Y. Corn Syrup 42 dextrose equivalent | 20.00 | 20.00 | 20.00 |
| Appropriate Buffer Solution (see text) | 10.00 | 10.00 | 10.00 |
| Sodium Bisulfite | — | 0.391 | — |
| Formalin (37% formaldehyde) | — | 0.335 | — |
| Sodium Hydroxymethane sulfonate | — | — | 0.50 |
| Distilled Water | 30.00 | 29.274 | 29.50 |
| | 100.00% | 100.000% | 100.00% |

*Combined mix represents a mixture of formalin and sodium bisulfite added separately. The quantities of formaldehyde and sodium bisulfite used are equivalent to the number of moles of NaCH$_3$OSO$_3$ used in the example above.

The parameters tested were the various preservative compositions, pH ranges and temperatures. The resultant color development measured by a standard Hellige Comparator using color disc Varnish (#620C-4) in ranges 1–9 and 9–18 are shown in Table VI below.

Three pH ranges which include most cosmetic products were selected for these tests, i.e. pH 4.0 covering underarm antiperspirants; pH 7.2 covering shampoos and most other cleansing preparations and pH 9.5 covering hair waving lotions, etc. Buffer systems were prepared essentially according to McIhlvane's tables in the "Handbook of Chemistry & Physics", 40th Edition and adjustments in pH, where necessary, were conventionally made by using NaOH or phosphoric acid. The results of these tests are shown in Table VI.

TABLE VI

COLOR EFFECT OF VARIOUS PARAMETERS ON PROTOTYPE SHAMPOOS

Data obtained on Hellige Comparator using color disc Varnish (#620C-4) ranges 1-9 and 9-18. The higher the number, the darker brown is the solution; conversely, the smaller the number, the paler is the solution. Initially, all solutions were colorless and were therefore rated 0 on the Comparator.

| pH | Compositions | 125° C. | 105° F. | Room Temperature |
|---|---|---|---|---|
| 9.5 | Blank (No preservatives) | 13 | 10-11 | 7 |
| | Combined Mix (Formalin & NaHSO$_3$) | 12 | 5 | 3 |
| | Sodium Hydroxymethane sulfonate | 8 | 2 | 1 |
| 7.2 | Blank (No preservatives) | 9-10 | 6 | 2 |
| | Combined Mix (Formalin & NaHSO$_3$) | 4 | 2 | 0-1 |
| | Sodium Hydroxymethane Sulfonate | 2 | 0-1 | 0* |
| 4.0 | Blank (No preservatives) | 3 | 1 | 0-1 |
| | Combined Mix (Formalin & NaHSO$_3$) | 1 | 0* | 0 |
| | Sodium Hydroxymethane Sulfonate | 1 | 0* | 0 |

*Hellige comparator does not distinctly differentiate in this range.

The results clearly prove the superiority of sodium hydroxymethane sulfonate over equivalent concentration of formaldehyde and sodium bisulfite added separately at a pH of about 7 and above. Also clearly seen were the effects of the presence of bisulfite over a blank sample containing no antioxidant.

As a further illustration of the superior effect of sodium hydroxymethane sulfonate over an equivalent mixture of sodium bisulfite and formalin, the progress of browning reaction and microbial contamination was monitored using the cream formulation of Table IV at three different temperatures, viz., room temperature, 105° F. and 125° F. and over various aging periods, viz., 12 days and 25 days. The color development in the cream was compared with a standard Pantone Color Specifier System for flat, opaque surfaces (published by Pantone, Inc. 1963, 55 Knickerbocker Rd., Moonachie, NJ) and the corresponding color number designated to the experimental cream samples. The results of such a study are shown in Table VII.

TABLE VII

EFFECT OF TEMPERATURE AND AGING ON CREAM APPEARANCE

| Aging | Temperature | Control (Blank) | Combined Mix | NaCH$_3$OSO$_3$ |
|---|---|---|---|---|
| Initial | | Greyish, off white (<100U) | Greyish, off white (<100U) | Greyish, off white (<100U) |
| 12 days | 125° F. | Brownish (466U) | Yellowish (155U) | Greyish, off white (<468U) |
| | 105° F. | Greyish, off white (468U) | off white (460U) | slightly off white (461C) |
| | Room Temperature | off white, frothing & overflowing (461C) | off white (100U) | slightly off white (<100U) |
| 25 days | 125° F. | Brown (>466U) | Grey, off white (468U) | Greyish, off white (<468U) |
| | 105° F. | Grey, Buff (>468U) | off white (>460U) | white (461C) |
| | Room Temperature | off white, frothing & overflowing (>461C) | off white (100U) | slightly off white (<100U) |

Numbers in parentheses represent the corresponding matching color in the Pantone Color Specifier.

The data again confirm the efficacy and superiority of sodium hydroxymethane sulfonate over a mixture of equivalent concentration of formalin and sodium bisulfite added separately. Sodium hydroxymethane sulfonate not only inhibited frothing and overflowing of the cream observed in the control samples, probably due to microbial contamination and fermentation, but also checked the development of browning due to the Maillard reaction.

Although the exact mechanism for the observed effectiveness is not known, it is believed, without being bound to any particular theory, that the superiority of the preservative effect of sodium hydroxymethane sulfonate, as mentioned earlier, is probably due to the slow hydrolysis of this compound in alkaline to neutral media with a gradual release of formaldehyde and sodium bisulfite.

It will be understood that the foregoing examples and explanations are for illustrative purposes only and that in view of the instant disclosure, various modifications of the present invention will be apparent to those skilled in the art and are to be included within the spirit and purview of this application and the scope of the appended claims.

I claim:
1. A cosmetic composition susceptible to degradation due to bacterial action and to browning due to the Maillard reaction which comprises:
   (a) a hydroxymethane sulfonate salt in an amount sufficient to produce a preservative effect simultaneously against said bacterial action and said browning wherein the cation of said salt is selected from the group consisting of sodium, potassium, ammonium and mixtures thereof; and
   (b) an aqueous cosmetic formulation having a pH value of about 7.0 to 9.5.
2. A cosmetic composition susceptible to degradation due to bacterial action and to browning due to the Maillard reaction which comprises:
   (a) sodium hydroxymethane sulfonate in an amount sufficient to produce a preservative effect simultaneously against said bacterial action and said browning; and
   (b) an aqueous cosmetic formulation having a pH value of about 7.0 to 9.5.
3. A composition as recited in claim 1 or 2 wherein said formulation has corn syrup as an ingredient.
4. A composition as recited in claim 1 or 2 wherein said amount of sodium hydroxymethane sulfonate is from about 0.01 to about 3.0%.
5. A method for substantially preserving an aqueous cosmetic from degradation due to bacterial action and from browning due to the Maillard reaction comprising treating said cosmetic with a sufficient amount of sodium hydroxymethane sulfonate to effect said preservation when the pH of said cosmetic is about 7.0 to 9.5.
6. A method as recited in claim 5, wherein said cosmetic has corn syrup as an ingredient.
7. A method as recited in claim 5 wherein said amount of sodium hydroxymethane sulfonate is from about 0.01 to about 3.0%.